(12) United States Patent
Boele et al.

(10) Patent No.: US 7,592,472 B2
(45) Date of Patent: Sep. 22, 2009

(54) PROCESS FOR THE PREPARATION OF MONOALKYLTIN TRIHALIDES AND DIALKYLTIN DIHALIDES

(75) Inventors: Maarten Boele, Goes (NL); Berth-Jan Deelman, Kapelle (NL); Gerard Van Koten, Den Dolder (NL); Erika Monika Wagner, Utrecht (NL)

(73) Assignee: Arkema Vlissingen (NL)

( * ) Notice: Subject to any disclaimer, the term of this patent is extended or adjusted under 35 U.S.C. 154(b) by 120 days.

(21) Appl. No.: 11/995,259

(22) PCT Filed: Jul. 11, 2006

(86) PCT No.: PCT/EP2006/064098
§ 371 (c)(1),
(2), (4) Date: Jan. 10, 2008

(87) PCT Pub. No.: WO2007/006783
PCT Pub. Date: Jan. 18, 2007

(65) Prior Publication Data
US 2009/0131704 A1    May 21, 2009

Related U.S. Application Data

(60) Provisional application No. 60/723,592, filed on Oct. 4, 2005.

(30) Foreign Application Priority Data
Jul. 12, 2005    (EP) .................................. 05076591

(51) Int. Cl.
*C07F 7/22* (2006.01)
(52) U.S. Cl. ........................................ 556/95; 556/103
(58) Field of Classification Search .................. 556/95, 556/103
See application file for complete search history.

(56) References Cited

U.S. PATENT DOCUMENTS

| 3,059,012 | A | * | 10/1962 | Hechenbleikner et al. ..... 556/95 |
| 3,085,102 | A | | 4/1963 | Yatagai et al. |
| 3,251,871 | A | * | 5/1966 | Dorfelt ........................ 556/103 |
| 3,287,386 | A | | 11/1966 | Neumann |
| 3,340,283 | A | | 9/1967 | Gloskey |
| 3,519,665 | A | * | 7/1970 | Hechenbleikner et al. ..... 556/99 |
| 3,519,667 | A | | 7/1970 | Molt et al. |
| 3,595,892 | A | * | 7/1971 | van den Hurk ................ 556/99 |
| 3,607,892 | A | | 9/1971 | Reifenberg et al. |
| 3,607,893 | A | | 9/1971 | Reifenberg et al. |
| 3,894,066 | A | | 7/1975 | Buschoff et al. |
| 3,994,944 | A | | 11/1976 | Buschhoff et al. |
| 4,044,035 | A | | 8/1977 | Bulten et al. |
| 4,046,791 | A | | 9/1977 | Matsuda et al. |
| 4,049,689 | A | | 9/1977 | Verbeck et al. |
| 4,080,362 | A | | 3/1978 | Huttin et al. |
| 4,105,684 | A | | 8/1978 | Hutton et al. |
| 4,130,573 | A | | 12/1978 | Hutton et al. |
| 4,202,830 | A | | 5/1980 | Korbanka et al. |
| 4,510,095 | A | * | 4/1985 | Holland et al. ................ 556/84 |
| 5,055,603 | A | * | 10/1991 | Ruf ............................ 556/102 |
| 6,768,017 | B2 | * | 7/2004 | Thoonen et al. ............... 556/97 |
| 6,846,944 | B2 | * | 1/2005 | Schumacher et al. ........ 556/104 |

FOREIGN PATENT DOCUMENTS

| CA | 1069129 | 1/1980 |
| EP | 0011280 | 11/1979 |
| GB | 1146345 | 3/1969 |

OTHER PUBLICATIONS

R.E. Hutton et al., Substituted Alkyltin Halides, J. Organomet. Chem., 156,1978, 369-382.
V.G. Kumar et al., A Convenient Synthesis of Monoctyltin(IV) Compounds From 1-,2-, or 3-Octenes, J. Organomet. Chem., 321, 1987, pp. 335-338.
E.J. Bulten, A Convenient Synthesis of (c1-C18) Alkyltin Trihalides, J. Organomet. Chem., 97, 1975, pp. 167-172.
M. Lautens et al., Regioselective Palladium-Catalyzed Hydrostannylation of Unsymmetrical Oxabicyclic Alkenes, Angew. Chem. Int. Engl., 1996, 35, No. 4, pp. 442-445.
J.W. Burley et al., Beta-Substituted Alkyltin Halides, J. Organomet. Chem., 170,1979, pp. 21-37.
J.W. Burley et al., Synthesis of Ketoalkyltin Chlorides via In-Situ Condensation and Hydrostannation of Ketonic Substrates, J. Organomet. Chem., 277, 1984, pp. 37-46.

* cited by examiner

*Primary Examiner*—Porfirio Nazario Gonzalez
(74) *Attorney, Agent, or Firm*—Steven D. Boyd

(57) ABSTRACT

The present invention relates to a process for the production of monoalkyltin trihalides of the formula $RSnHal_3$, in which R=alkyl or cycloalkyl and Hal=Cl. Br or I. Said process comprises contacting the corresponding alkene or cycloalkene, stannous halide $SnHal_2$, hydrogen halide HHal and optionally Sn metal, in the presence of at least one transition metal-based catalyst, thereafter isolating the monoalkyltin trihalides from the medium. The present invention also relates to a process for the production of dialkyltin dihalides of the formula $R_2SnHal_2$ from monoalkyltin trihalides of the formula $RsnHal_3$'. in which R=alkyl or cycloakyl and Hal=Cl, Br or I. Said process comprises contacting monoalkyltin trihalides $RsnHal_3$ and Sn metal, optionally thereafter isolating the dialkyltin dihalides $R_2SnHal_2$ from the medium.

27 Claims, No Drawings

PROCESS FOR THE PREPARATION OF MONOALKYLTIN TRIHALIDES AND DIALKYLTIN DIHALIDES

FIELD OF THE INVENTION

Monoalkyltin trihalides, by way of example, monoalkyltin trichlorides $RSnCl_3$ (R being $C_nH_{2n+1}$) particularly methyl-, butyl- and octyltin trichloride, are industrially important as intermediates for PVC stabilizers, glass coating chemicals and catalysts. A new route to produce monoalkyltin trihalides with $n \geq 2$ has been discovered. The method utilizes the corresponding alkene, tin dihalide and hydrogen halide as raw materials and a transition metal complex as the catalyst. The reaction proceeds smoothly and selectively under mild conditions. The monoalkyltin trihalides either isolated from the reaction medium either coming from another source are reacted with tin metal to get a mixture of tin dihalide and dialkyltin dihalides.

THE PRIOR ART AND THE TECHNICAL PROBLEM

Monoalkyltin trichlorides and dialkyltin dichlorides are currently prepared through multistep processes. In these processes, the monoalkyltin trichlorides and dialkyltin dichlorides are formed as a mixture by disproportionation of the corresponding tetraalkyltin compound $R_4Sn$ with $SnCl_4$. The tetraalkyltin compound is prepared by reacting trialkylaluminium or alkyl-Grignard reagents with $SnCl_4$. This route suffers from rather high raw material costs. Moreover, the product composition depends on the length of the alkyl chain and reaction conditions, and is therefore hardly adjustable to the actual demand. Fractionation by distillation may be required but becomes practically impossible for higher alkylchains (n=8 or longer). Therefore, alternative methods for the selective production of monoalkyltin trichlorides and dialkyltin dichlorides are highly desirable.

Alternative methods to prepare dialkyltin dichlorides include the selective dialkylation of tin tetrahalide using alkylaluminium reagents (see GB Pat 923179, DE 1157617), or reaction of organic chloride with metallic tin. The latter reaction usually requires a catalyst, for example magnesium, copper (see U.S. Pat. No. 3,085,102) or hexamethylphosphoric triamide (HMPT, see U.S. Pat. Nos. 4,049,689, 4,044,035). The low yields for higher alkyl chlorides and large amounts of catalyst needed make these methods generally unattractive from a commercial point of view.

It is known that the reaction of $SnCl_4$ with trialkylaluminum etherate $R_3Al(OR'_2)$/amide $R_3Al(NR'_3)$ compounds or alcoholates $R_2Al(OR')$ allows the formation of $RSnCl_3$. Similarly, mixtures of monoalkyltin trichlorides and dialkyltin dichlorides have been prepared in one step from $SnCl_4$ using $R_3Al$ and an excess of ether. This is described in the following patents U.S. Pat. No. 3,894,066, U.S. Pat. No. 3,994,944, and patent application US 2004/0133022A1. Drawback of these procedures is the excess of alkylaluminiums often required to achieve good yields.

EP 1 225 177 describes a process for the production of monoalkyltin trihalides of the formula $RSnX_3$, wherein R=alkyl or cycloalkyl and X=Cl, Br or I, involving a redistribution reaction between tetraorganotins, triorganotin halides or diorganotin halides and tin tetrahalides, said process comprising contacting tetra- ($R_4Sn$), tri- ($R_3SnX$) or diorganotin halides ($R_2SnX_2$) with $SnX_4$ to afford said monoorganotin trihalides in the presence of at least one transition metal complex, said complex comprising at least one transition metal, M, selected from Group VIII of the periodic Table of elements, at least one monodentate ligand or bidentate ligand, L, L' or L", and optionally one or more anions, X, of an organic or inorganic acid, as a catalyst or catalyst precursor. This reaction still requires the production of the initial tetraorganotins, triorganotin halides or diorganotin halides from tin tetrahalide and suffers from the formation of tin dihalide as byproduct.

An alternative route to monoalkyltin trichlorides is the reaction of the corresponding alkylhalide with $SnCl_2$ using a catalyst. Useful catalysts are phosphonium halides, amines or phosphines, disulfides, Se(II) or metal salts of group 1-3, (e.g. LiCl or $MgCl_2$), or Mg metal with $I_2$ These reactions generally require high temperatures. This is described in the following patents U.S. Pat. No. 3,519,667, U.S. Pat. No. 3,340,283, CA 1069129, GB 1,146,435, U.S. Pat. No. 4,046,791. Trialkylantimony compounds were found to be effective as catalysts in the case of alkyltin tribromides, but the lack of reactivity for the alkyltin trichlorides and the toxicity of the trialkylantimony catalysts renders this route less useful (E. J. Bulten, *J. Organomet. Chem.* 1975, 97, 167).

Reaction of α-olefins with stannane $SnH_4$ has been reported using a free radical catalyst (e.g. alkyl peroxides and cobalt naphthenate). The cryogenic conditions and low yields make this procedure unattractive from an industrial point of view. It has been described in GB 1,255,859. Addition of unactivated alkenes to $HSnX_3$ yielding $RSnX_3$ has been described to occur through a similar mechanism, but these produce the secondary substituted monoalkytin trihalides in poor yields. It has been described in U.S. Pat. No. 3,607,893. Hydrostannylations are known to occur when trialkyltin hydrides are reacted with substrates containing multiple bonds under radical conditions. Examples also exist where complexes of rhodium and palladium are successfully applied to catalyse the addition of trialkyltin hydrides to alkynes and alkenes to give mixed tetraorganotin compounds (M. Lautens, W. Klute, *Angew. Chem. Int. Ed. Engl.* 1996, 35, 442 and references therein).

The preparation of organotin compounds directly from $SnCl_2$ (or, alternatively, Sn metal), HCl and the corresponding alkene represents an attractive alternative route to monoalkyltin trihalides. Its main advantages stem from the low raw material costs and ability to produce the desired alkyltin chloride selectively in one step. This reaction has been reported before for α,β-unsaturated carbonyl-containing substrates where it occurs without a catalyst under mild conditions. The carbonyl functionality acts as an activating group for the conversion in these substrates. Both monoorganotin trihalides and diorganotin dihalides or mixtures thereof have been produced. It has been described in U.S. Pat. No. 4,105,684, EP 0,011,280, U.S. Pat. No. 4,080,362, U.S. Pat. No. 4,130,573, J. W. Burley, P. Hope, R. E. Hutton, C. J. Groenenboom, *J. Organomet. Chem.* 1979, 170, 21, U.S. Pat. No. 4,202,830, J. W. Burley, P. Hope, A. G. Mack., *J. Organomet. Chem.* 1984. However, unactivated alkenes are not reactive under these conditions. Reaction of 1-octene with $HSnCl_3$ $(Et_2O)_2$ reportedly only results in trace amounts (<1%) of sec-octyltin trichloride (277, 37, R. E. Hutton, J. W. Burley, *J. Organomet. Chem.* 1978, 156, 369). n-Octyltin trichloride was formed in up to 81% yield when $[(\eta^5-C_5H_5)_2Zr(H)Cl]$ and a stoichiometric amount of 1-octene were reacted with 0.5 equivalent of $SnCl_4$ at room temperature. Obviously, the need for large amounts of zirconium reagent makes this route industrially less attractive (V. G. Kumar Das, O. Ghee Chee, *J. Organomet. Chem.* 1987, 321, 335).

A novel process for the direct and selective preparation of monoalkyltin trihalides from the corresponding unactivated alkene (e.g. 1-octene), stannous halide (e.g. SnCl$_2$) and hydrogen halide (e.g. HCl) in one single reaction step in the presence of a transition metal complex as a catalyst has been found. The reaction proceeds selectively, the only significant side product being isomerised alkene. Dialkyltin dihalides are then produced from monoalkyltin trihalides.

BRIEF DESCRIPTION OF THE INVENTION

The present invention comprises a process for the production of monoalkyltin trihalides of the formula RSnHal$_3$, in which R=alkyl or cycloalkyl and Hal=Cl, Br or I, said process comprising contacting alkene, stannous halide and hydrogen halide in the presence of at least one transition metal complex as a catalyst or catalyst precursor; optionally thereafter isolating the monoalkyltin trihalides from the medium. In a preferred embodiment of the invention said complex comprises at least one transition metal M, at least one monodentate ligand or bidentate ligand, L or L', and optionally one or more anions, X, being defined as (i) the conjugate base of an organic or inorganic acid, (ii) a hydride or (iii) a hydrocarbyl fragment. In another preferred embodiment of the invention said complex is a transition metal salt consisting of transition metal M, and optionally one or more anions, X, being defined as the conjugate base of an organic or inorganic acid, and optionally one or more alkalimetal cations.

Advantageously M is selected from Group VIII of the periodic Table of elements. The reaction can be carried out with or without a solvent.

The reaction proceeds selectively, the only significant side product being alkene isomers resulting from isomerisation of the starting alkene. The alkene is currently applied in excess to the other reactants. The hydrogen halide acid may be employed as gas or in solution. The reaction proceeds smoothly at room temperature or above. A multitude of organic solvents can be used, in particular, solvents like alcohols, ethers and apolar aromatic and aliphatic solvents and mixtures thereof. Small amounts of water do not disturb the reaction.

The invention also comprises a process to make dialkyltin dihalides. The monoalkyltin trihalides (i) either isolated from the above reaction medium (ii) either coming from another source are reacted with tin metal to get a mixture of tin dihalide and dialkyltin dihalides. Optionally in option (i) the tin metal can be added during the reaction to monoalkyltin trihalide. In that way the tin dihalide formed can be consumed to produce monoalkyltin trihalide.

The invention also relates to the use of these monoalkyltin trihalides, dialkyltin dihalides and mixtures thereof made according to the process hereabove as intermediates for PVC stabilizers, glass coating chemicals and catalysts. The invention also relates to the PVC stabilizers, glass coating chemicals and catalysts having been made from the monoalkyltin trihalides and dialkyltin dihalides made by the process of the present invention.

DETAILED DESCRIPTION OF THE INVENTION

The present invention relates to a process for the production of monoalkyltin trihalides of the formula RSnHal$_3$, in which R=alkyl or cycloalkyl and Hal=Cl, Br or I. Said process comprises contacting the corresponding alkene or cycloalkene, stannous halide SnHal$_2$, hydrogen halide HHal and optionally Sn metal, in the presence of at least one transition metal-based catalyst, thereafter isolating the monoalkyltin trihalides from the medium.

Advantageously, R is an alkyl, linear or branched, in the range C2-C20 and preferably selected among C2, C3, C4, C5, C6, C7 and C8.

As regards the monoalkyltin trihalides, in a specific embodiment Hal is chloride. This means that the stannous halide is SnCl$_2$ and hydrogen halide is HCl. In the formula RSnHal$_3$ the group R is preferably defined as an alkyl (linear or branched) or cycloalkyl having from 2 to 20 carbon atoms. Preferably n-butyl, butyl, n-hexyl, hexyl, n-octyl and octyl are used.

As regards the alkene (sometimes called olefin), it can be described, by way of example, as the following formula:

and the reaction route as follows (eq 1):

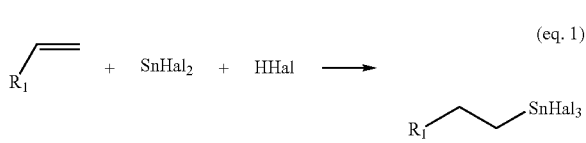

(eq. 1)

in which R$_1$ is H or is defined as an alkyl (linear or branched or substituted). having from 1 to 18 carbon atoms.

The alkene, but also cycloalkene, has advantageously from 2 to 20 carbon atoms. In a specific embodiment the alkene also can be described as R$_1$(R$_2$)C=C(R$_3$)(R$_4$) with R$_1$-R$_4$ being any alkyl group (branched or linear or substituted) or hydrogen, R$_1$, R$_2$, R$_3$ and/or R$_4$ being optionally linked to any of the other R groups, for example R$_1$ or R$_2$ being linked to R$_3$ or R$_4$, or R1 being linked to R2, and the number of carbon atoms in R$_1$-R$_4$ ranging from 0 to 18.

The olefin can contain functions and/or substituents. Advantageously this hydrocarbon has 4 to 8 carbon atoms. Especially 1-butane and 1-octene are relevant to produce industrially important organotins.

As regards stannous halide, it can be SnHal$_2$ or any precursor. Mention may be made, by way of examples, of Sn/SnHal$_4$ blends and HHal/Sn. The precursor also relates to SnHal$_2$/Sn/SnHal$_4$ blends. The stannous halide is preferably anhydrous but also their aqua complexes can be used. The stannous halide SnHal$_2$ can be produced in situ. According to a specific embodiment, SnHal$_2$ can be partly or totally replaced by a Sn/SnHal$_4$ blend (1/1 ratio) producing SnHal$_2$ in situ.

As regards the hydrogen halide, it can be the hydrogen halide itself as gas or solution in a solvent or any precursor or any blend thereof. The precursor can be [HN(alkyl)3]Hal, another ammonium salt or other Lewis base adduct of hydrogen halide. When used as gas the hydrogen halide may be diluted with another gas. In a preferred embodiment of the invention the hydrogen halide can be HCl or [HN(C$_2$H$_5$)$_3$]Cl. In another preferred embodiment, Hal is chloride, the stannous halide is SnCl$_2$ and hydrogen halide is HCl.

As regards the catalyst, in its broadest form the catalyst is a transition metal-based catalyst.

According to a first embodiment of the invention, said transition metal-based catalyst can be a complex, said complex comprising at least one transition metal M, at least one monodentate ligand L or bidentate ligand L', and optionally one or more anions X, X being defined as (i) the conjugate base of an organic or inorganic acid, (ii) a hydride or (iii) a hydrocarbyl fragment.

Advantageously, the catalyst is a complex having the formula $$L'MX_2 \quad (I)$$

wherein L' is a bidentate ligand, or $$L_2MX_2 \quad (II)$$

or $$[LMX_2]_2 \quad (III)$$

or $$L_4M \quad (IV)$$

wherein L is a monodentate ligand.

Preferably, the complex is $M(PPh_3)_4$.

According to a second embodiment of the invention, the transition metal-based catalyst can be a transition metal salt consisting of transition metal M, and optionally one or more anions, X, being defined as the conjugate base of an organic or inorganic acid, and optionally one or more alkalimetal cations.

More preferably, the transition metal-based catalyst can be a salt, said salt consisting of transition metal M, one or more anions X, X being defined as the conjugate base of an organic or inorganic acid, and optionally one or more alkalimetal cations M', such as $Li^+$, $Na^+$ or $K^+$, and/or one or more protons.

Advantageously, the salt is chosen from the group consisting of $MX_2$, $M'_2MX_4$ and $H_2MX_4$. For example, $M(Hal)_2$ or $K_2MX_4$ can be employed.

According to a third embodiment of the invention, the transition metal-based catalyst can be a supported transition metal M in its zero valent oxidation state.

Preferably, said support is carbon.

Regardless of the type of the transition metal-based catalyst used within the framework of the present invention, i.e. a complex, a salt or a supported transition metal M, the transition metal M to be used is advantageously a Group VIII metal (also called columns 8-10), and preferred metals are Pt, Pd and/or Ni. The groups X may be anions of organic and/or inorganic nature, hydrogen or a hydrocarbyl fragment. In the catalyst species containing two X's (by way of example like $L_2M(R)Cl$) the two X's can be mutually different. It is preferred to use Cl, Br, I, acetate, triflate, tosylate, hydride or alkyl. In a preferred embodiment of the invention L in formula (II) or (III) is selected from phosphine, alkene, amine, pyridine, organic sulfide, nitrile and imidazoline-2-ylidene. L' is selected from phosphine containing ligand with additional O or N, diphosphonic, dialkene, diamine and bis(imidazoline-2-ylidene) ligands. More in particular L is triphenylphosphine or L'=N,N, N',N'-tetramethylethylenediamine (TMEDA), or bypridine (optionally substituted), M is Pd or Pt and for catalyst (I), X is Cl. In a specific embodiment catalysts are choosen among $Pd(PPh_3)_4$ and $Pt(PPh_3)_4$.

As regards the solvent, in general organic, aprotic or even protic solvents are preferred, especially aromatic solvents, chloroaromatic solvents, alkanes, ethers and alcohols. In particular tetrahydrofuran (THF), ethanol and 1,2-dimethoxyethane (DME) were found to be appropriate solvents.

As regards the operating conditions and the proportions, the reaction is made continuously or in batch. The batch process is preferred. Temperature can be, by way of example, from ambient to 200° C. A range from 20 to 130° C. is advantageous. As regards the pressure, no pressure is necessary except to maintain the alkene, when it has a low boiling point, and hydrogen halide in the reaction medium. However, to speed up the reaction higher pressures may be advantageous. Preferred reaction times range from a few seconds to 48 hours. The molar ratio of olefin to $SnHal_2$ falls within the range 0.1/1 to 200/1, more advantageously 1/1 to 100/1. The molar ratio of HHal to $SnHal_2$ falls within the range 0.01/1 to 100/1. The catalyst loading (molar percentage of M) based on the number of moles of $SnHal_2$ can be 0.001 to 5%, more preferred 0.1 to 1.5%. Should a solvent be used, any proportion is convenient. The reaction is carried out in any usual apparatus. The reaction can be checked by taking samples and conventional analysis. The monoalkyltin trihalides can be separated from the reaction medium by any means such as, by way of examples, distillation, solvent extraction, crystallization.

About the yield based on olefin:

a1 is the number of moles of olefin originally present at the beginning of the reaction, a2 is the number of moles of olefin converted, a3 is the number of moles of olefin converted to monoalkyltin trihalide, the yield based on olefin is defined as the ratio a3/a1 and typically is in the range 1-80%. The selectivity based on olefin is defined as a3/a2 and is typically in the range 10-80%.

About the Sn yield:

b1 is the number of moles of Sn (present as Sn, $SnHal_2$ or SnHal4) at the beginning of the reaction, b2 is the total number of moles of Sn (present as Sn, $SnHal_2$ and $SnHal_4$) converted.

b3 is the number of moles of monoalkyltin trihalide produced.

The Sn selectivity is defined as the ratio b3/b2 and is in the range 95-100%.

The Sn yield is defined as b3/b1. The conversion is defined as b2/b1.

Also ratios $Sn/SnHal_4 > 1$ can be used. Optionally Sn can be added to the reaction mixture in the course of reaction. In this case the excess Sn metal gives rise to dialkyltin dihalide and $SnHal_2$ according to the following overall reaction stoichiometry:

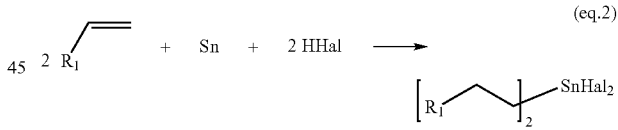

(eq.2)

In eq 2 the alkene is only an example, it is clear that eq 2 concerns any alkene as described above.

$$2RSnHal_3 + Sn \rightarrow R_2SnHal_2 + 2SnHal_2 \quad (eq. 3)$$

The $SnHal_2$ is entering the reaction of eq. 1 affording another equivalent of $RSnHal_3$.

As regards the conversion, yields and selectivities a4 is the amount of olefin in moles converted to dialkyltin dihalide, b4 is the number of moles of dialkyltin dihalide produced.

The conversion, yields and selectivities are now defined as follows:

The olefin yield is defined as (a3+a4)/a1.

The olefin selectivity is defined as (a3+a4)/a2

The Sn yield is defined as (b3+b4)/b1. The conversion is defined as above.

The Sn selectivity is defined as the ratio (b3+b4)/b2.

Finally the two reactions of eq 1 and eq 3 can also be carried out as two consecutive reactions. In this case the monoalkyltin trihalide RSnHal$_3$ is first produced. The next step is then performed by adding Sn metal to the reaction mixture. The stannous halide that is left after isolation of the RSnHal$_3$ and R$_2$SnHal$_2$ products can be recycled to the first step. By chosing the Sn/RSnHal$_3$ stoichiometry any R$_2$SnHal$_2$/RSnHal$_3$ ratio in the product mixture can be chosen.

The present invention also relates to a process for the production of dialkyltin dihalides of the formula R$_2$SnHal$_2$ from monoalkyltin trihalides of the formula RSnHal$_3$, in which R=alkyl or cycloalkyl and Hal=Cl, Br or I, said process comprising contacting monoalkyltin trihalides RSnHal$_3$ and Sn metal, optionally thereafter isolating the dialkyltin dihalides R$_2$SnHal$_2$ from the medium.

Advantageously, R is an alkyl linear or branched, in the range C1-C20 and preferably selected among C2, C3, C4, C5, C6, C7 and C8.

In a preferred embodiment, the monoalkyltin trihalides RSnHal$_3$ are produced by the process above-described As regards the process to make dialkyltin dihalides from tin and monoalkyltin trihalides, the monoalkyltin trihalides (i) either isolated from the above reaction medium (ii) either coming from another source are reacted with tin metal to get a mixture of tin dihalide and dialkyltin dihalides, according to the following reaction:

2RSnHal$_3$+Sn→R$_2$SnHal$_2$+2SnHal$_2$     (eq. 3)

The reaction proceeds typically in the temperature range of 20 to 150° C. with or without a catalyst and can be run with or without solvent. If solvent is applied, preferred solvents are organic apolar aliphatic or aromatic solvents or protic solvents or mixtures thereof. Water has a beneficiary effect on the reaction. Advantageously, the SnCl$_2$ formed may be isolated and recycled, for example by extraction with water followed by drying, and applied as the starting material for the monoalkyltin trihalides production process as described above. By choosing the Sn/RSnHal$_3$ stoichiometry, any R$_2$SnHal$_2$/RSnHal$_3$ ratio in the product mixture can be chosen. In other words, by simply adjusting the amount of Sn, different mixtures of monoalkyltin trihalides and dialkyltin dihalides can be prepared.

Particularly, if an amount of Sn metal is added in deficiency, a partial conversion of the monoalkyltin trihalides RSnHal$_3$ occurs and a mixture that contains both monoalkyltin trihalides and dialkyltin dihalides is consequently obtained. In practice, such a "ready-to-go" mixture is currently used for making stabilizers.

Of course, the process of the present invention may further comprise a step of isolating the dialkyltin dihalides R$_2$SnHal$_2$ from the medium, in particular from the monoalkyltin trihalides and dialkyltin dihalides mixture.

EXAMPLES

Example 1

A reaction vessel equipped with magnetic stirring was brought under inert atmosphere and charged with 62 mg of Pt(0)(PPh$_3$)$_4$ and 138 mg of HNEt$_3$Cl (1.0 mmol). This mixture was then suspended by adding 0.5 mL of THF, followed by 1.0 mL of 1-octene and 0.5 mL of a 0.4 M solution of anhydrous SnCl$_2$ in THF (0.20 mmol). The vessel was placed in an oil bath and heated to 80° C. and stirred for 16 hours.

After cooling down to room temperature, the liquid phase was ethylated with excess EtMgCl, and analyzed by GLC using an internal standard. The yield is 10.5 mg (0.031 mmol; b3/b1=16%) of monooctyltin trichloride

Example 2

A reaction vessel equipped with magnetic stirring was brought under inert atmosphere and charged with 5.0 mg of Pd(PPh$_3$)$_4$. Next, 1.0 mL of a 0.8 M solution of anhydrous SnCl$_2$ in THF (0.80 mmol) was added, followed by 2.0 mL of 1-octene (12.5 mmol). The vessel was placed in an oil bath and heated to 60° C. Subsequently, 1.5 mL of a 0.25 M HCl solution in THF (0.375 mmol) was slowly added and the resulting pale yellow solution was stirred for 1 hr. at 60° C. After the reaction, the solvent and excess 1-octene were removed in vacuo to yield an orange/red residu. This residu was suspended in 3.0 mL of toluene and the resulting suspension stirred vigorously for several minutes. The liquid phase was analyzed by GLC after ethylation with excess EtMgCl. The yield is 112 mg (0.33 mmol; b3/b1=41%) of monooctyltin trichioride.

Example 3

A reaction vessel equipped with magnetic stirring was brought under inert atmosphere and charged with 9.5 mg of Pd(PPh$_3$)$_4$ and 172 mg SnCl$_2$ (0.91 mmol). Next, 4 mL of THF were added. The vessel was placed in an oil bath and heated to 50° C., while propylene was bubbled through the solution. Subsequently, 4.0 mL of a 0.20 M HCl solution in THF (0.80 mmol) was slowly added and the resulting pale yellow solution was stirred for 1.5 hr. at 50° C. with propylene bubbling through the solution.

After the reaction, propylene bubbling was stopped and the solvent was removed in vacuo to yield an orange/red residue. This residu was suspended in 3.0 mL of toluene and the resulting suspension stirred vigorously for several minutes. The liquid phase was analyzed by GLC, using an internal standard, after ethylation with excess EtMgCl. The yield is 12.6 mg (0.047 mmol; b3/b1=6%) of monopropyltin trichloride.

Example 4

In a pressure vessel equipped with an inlet to enable dinitrogen purge and a stirring bar, 15.0 mg of Pd(PPh$_3$)$_4$ was weighed in. The tube was brought under inert atmosphere and subsequently cooled to −10° C. Next, 4 mL of liquid 1-butene was added, followed by 1.0 mL of a 0.8 M SnCl$_2$ solution in THF and dropwise addition of 3.0 mL of a 0.25 M HCl solution in THF. The vessel was then sealed and the cooling bath removed. When the vessel had reached room temperature, the vent was opened for a few seconds to remove the excess pressure that had built up. The mixture was subsequently stirred at room temperature for 64 hrs.

After the reaction, the slightly turbid yellow reaction mixture was transferred to a second flask. The resulting residue was worked-up, ethylated and analyzed by GLC as described for Example 2. The analysis showed the formation of 45 mg of butyltin trichloride (0.16 mmol; b3/b1=20%).

Example 5

A reaction vessel equipped with magnetic stirring was brought under inert atmosphere and charged with 15.0 mg of Pd(PPh$_3$)$_4$ and 38 mg SnCl$_2$. THF (1 mL) was added, followed by the addition of 3.0 mL of cyclohexene. Finally, 0.8 mL of a 0.20 M solution of HCl in THF was added dropwise by means of a syringe. After the addition was completed, the resulting mixture was heated to 60° C. and stirred for 24 hr. at this temperature.

After cooling down to room temperature, the volatiles were evaporated under reduced pressure. The resulting residue was worked-up, ethylated and analyzed by GLC as described for Example 2. The reaction yield was determine to be 4.0 mg (0.013 mmol; b3/b1=5%) of monocyclohexyltin trichloride.

Example 6

A reaction vessel equipped with magnetic stirring was brought under inert atmosphere and charged with 1 mL of a THF solution containing 4.5 mg of Pd(PPh$_3$)$_4$ and 75.1 mg SnCl$_2$ (0.40 mmol). The reaction vessel was heated to 50° C., after which 1.5 mL of styrene (13.1 mmol) was added. Subsequently, 2.0 mL of a 0.20 M HCl solution in THF (0.40 mmol) was slowly added and the resulting pale yellow solution was stirred for 16 hr. at 50° C.

After the reaction, the solvent and excess alkene were removed in vacuo to yield an orange/red residu. This residu was suspended in 3.0 mL of toluene and the resulting suspension stirred vigorously for several minutes. The liquid phase was analyzed by GLC, using an internal standard, after ethylation with excess EtMgCl. The yield is 5.9 mg (0.018 mmol; b3/b1=5%) of mono(phenylethyl)tin trichloride.

Example 7

A reaction vessel equipped with magnetic stirring was brought under inert atmosphere and charged with 1.7 mg PdCl$_2$ and 634 mg SnCl$_2$. Ethanol (2 mL) was added, followed by the addition of 4.4 ml of 1-octene. The mixture was heated to 50° C. and 0.91 mL of a 2.75 M solution of HCl in ethanol were added by means of a syringe. After the addition was completed, the reaction mixture was stirred for 44 h at 50° C.

After cooling down to room temperature, the volatiles were evaporated under reduced pressure. The resulting residue was worked-up, ethylated and analyzed by GLC as described for Example 2. The reaction yield was determined to be 500 mg (1.48 mmol; b3/b1=44%) of monooctyltin trichloride.

Example 8

A reaction vessel equipped with a magnetic stirring bar was charged with 10.8 mg Pd on activated carbon (10% Pd) and brought under inert atmosphere. The catalyst was then suspended by adding 2.0 mL of acetone. The mixture was heated up to 50° C. and 4.7 mL of 1-octene were added. In a separate reaction vessel, a mixture of 671 mg SnCl$_2$, 0.66 mL of a 4 M solution of HCl in water (2.65 mmol) and 10.5 mL acetone was prepared, which was added by means of a syringe to the initial reaction mixture. The resulting mixture was stirred for 20 hat 50° C.

After cooling down to room temperature, the volatiles were evaporated under reduced pressure. The resulting residue was treated as described for Example 2. A yield of 98 mg (0.29 mmol; b3/b1=8%) of monooctyltin trichloride was calculated from the results of the GLC measurements.

Example 9

A reaction vessel equipped with magnetic stirring was charged with 1.00 g Sn powder (8.42 mmol) and inertised.

Next, 5.0 mL of toluene was added, followed by 2.55 g of monobutytin trichloride (9.04 mmol). This mixture was stirred at 105° C. for 24 hrs.

After the reaction, the resulting light-grey suspension was cooled to room temperature and filtered. The remaining solids were extracted with 3 times 5 mL of toluene, and the combined organic fractions were evaporated to dryness. This resulted in 1.31 g white crystalline material as the product. Identification by $^1$H and $^{119}$Sn NMR, GLC (after ethylation with EtMgCl) and mp confirm the product to be >98% pure dibutyltin dichloride (4.31 mmol).

Example 10

A reaction vessel equipped with magnetic stirring was charged with 485 mg of Sn powder and brought under inert atmosphere. Next, 4.0 mL of toluene were added, followed by 1.41 g of octyltin trichloride. This mixture was stirred at 105° C. for 24 hrs.

After the reaction, the resulting off-white suspension was cooled to room temperature and filtered. The remaining solids were extracted with toluene, and the combined organic fractions were evaporated to dryness. This resulted in 0.80 g (1.92 mmol; (b3+b4)/b1=47%) of dioctyltin dichloride.

Example 11

A reaction vessel equipped with magnetic stirring was brought under inert atmosphere and charged with 15 mg of Pd(PPh$_3$)$_4$. Next, 238 mg of Sn powder was added, followed by 3 mL of THF and 5.0 mL of 1-octene. The vessel was placed in an oil bath and heated to 50° C. Subsequently, 3 mL of a 0.3 M HCl solution in THF were added slowly and the resulting pale yellow solution was stirred for 40 hrs under gentle reflux.

The solvent and the excess of 1-octene were removed in vacuo to yield an orange/red residue. This residue was suspended in 3.0 mL of toluene and the resulting suspension was stirred vigorously for several minutes. The liquid phase was analyzed by GLC after ethylation with excess EtMgCl. The yield was 50 mg (0.12 mmol: (b3+b4)b1=6%) of dioctyltin dichioride The monoalkyltin trihalides, dialkyltin dihalides and mixtures thereof made according to the processes hereabove described are currently used as intermediates for PVC stabilizers, glass coating chemicals and catalysts.

The invention claimed is:

1. Process for the production of monoalkyltin trihalides of the formula RSnHal$_3$, in which R is selected from alkyl or cycloalkyl and Hal is selected from Cl, Br or I, said process comprising contacting the alkenes or cycloalkenes corresponding to said monoalkyltin trihalides, stannous halide SnHal$_2$, hydrogen halide HHal and optionally Sn metal, in the presence of at least one transition metal M based catalyst, and thereafter isolating the monoalkyltin trihalides from the medium.

2. Process according to claim 1 wherein said at least one transition metal-based catalyst is a complex, said complex comprising at least one transition metal M, at least one monodentate ligand L or bidentate ligand L', and optionally one or more anions X selected from (i) the conjugate base of an organic or inorganic acid, (ii) a hydride or (iii) a hydrocarbyl fragment.

3. Process according to claim 2 wherein the complex is chosen from the group consisting of L$_2$MX$_2$, [LMX$_2$]$_2$, L$_4$M and L'MX$_2$.

4. Process according to claim 3 wherein the complex is $M(PPh_3)_4$.

5. Process according to claim 1 wherein said at least one transition metal-based catalyst is a salt, said salt consisting of transition metal M, one or more anions X selected from the conjugate base of an organic acid or inorganic acid, and optionally one or more alkali metal cations M'.

6. Process according to claim 5 wherein the salt is selected from the group consisting of $MX_2$, $M'_2MX_4$ or $H_2MX_4$.

7. Process according to claim 6 wherein the salt is $M(Hal)_2$.

8. Process according to claim 1 wherein said at least one transition metal-based catalyst is a supported transition metal M in its zero valent oxidation state.

9. Process according to claim 8 wherein the support is carbon.

10. Process according claim 1 wherein the transition metal M is a Group VIII metal.

11. Process according to claim 1 wherein the stannous halide $SnHal_2$ is produced in situ.

12. Process according to claim 11 wherein stannous halide $SnHal_2$ is partly or totally replaced by a blend of Sn and $SnHal_4$.

13. Process according to claim 1 wherein R is an alkyl, linear or branched, in the range C2-C20.

14. Process according to claim 1 wherein the reaction is carried out in a solvent.

15. Process according to claim 14 wherein the solvent is selected from aromatic solvents, chloroaromatics, alkanes, ethers and alcohols.

16. Process according to claim 1 wherein Hal is chloride, the stannous halide is $SnCl_2$ and hydrogen halide is HCl.

17. Process for the production of dialkyltin dihalides of the formula $R_2SnHal_2$, from monoalkyltin trihalides of the formula $RSnHal_3$, in which R is selected from alkyl or cycloalkyl and Hal is selected from Cl, Br or I, said process comprising contacting monoalkyltin trihalides $RSnHal_3$ and Sn metal, optionally thereafter isolating the dialkyltin dihalides $R_2SnHal_2$.

18. Process according to claim 17 wherein R is an alkyl, linear or branched, in the range C1-C20.

19. Process according claim 17 wherein the amount of Sn metal is added in deficiency.

20. Process according to claim 5 wherein said one or more alkali metal cation M' is selected from $Li^+$, $Na^+$, $K^+$, one or more protons or mixtures thereof.

21. Process according to claim 10 wherein said Group VIII metal is selected from Pt, Pd or Ni.

22. Process according to claim 12 wherein said blend of Sn and SnHal is at a 1/1 ratio.

23. Process according to claim 13 wherein said alkyl, linear or branched is selected from C2, C3, C4, C5, C6, C7 or C8 alkyls.

24. Process according to claim 14 wherein said solvent is selected from organic, aprotic or protic solvents.

25. Process according to claim 15 wherein said solvent is selected from tetrahydrofuran (THF), ethanol or 1,2-dimethoxyethane (DME).

26. Process according to claim 18 wherein said R is selected from C2, C3, C4, C5, C6, C7 and C8 allkyls.

27. Process according to claim 19 further comprising a step of isolating the dialkyltin dihalides $R_2SnHal_2$.

* * * * *